United States Patent [19]

Donnerhack et al.

[11] Patent Number: 4,688,603
[45] Date of Patent: Aug. 25, 1987

[54] INSULATED HOSE OF SYNTHETIC MATERIAL

[75] Inventors: Andreas Donnerhack, Krefeld; Detlef Jankowski, Duisburg; Kurt Pfeil-Schneider, Nettetal; Klemens Thoma, Krefeld-Huls; Wolfgang Volker, Tonisvorst, all of Fed. Rep. of Germany

[73] Assignee: Messer Griesheim GmbH, Fed. Rep. of Germany

[21] Appl. No.: 821,348

[22] Filed: Jan. 22, 1986

[30] Foreign Application Priority Data

Feb. 14, 1985 [DE] Fed. Rep. of Germany ....... 3505045

[51] Int. Cl.$^4$ .............................................. F16L 11/11
[52] U.S. Cl. .................................... 138/103; 138/121; 174/68 C
[58] Field of Search ............... 138/122, 125, 129, 149, 138/DIG. 10, 103, 121; 174/68 C

[56] References Cited

U.S. PATENT DOCUMENTS

| | | | |
|---|---|---|---|
| 2,561,891 | 7/1951 | Tucker | 138/DIG. 10 |
| 2,858,854 | 11/1958 | Daggett | 138/DIG. 10 |
| 2,861,598 | 11/1958 | Carder, Jr. et al. | 138/DIG. 10 |
| 3,240,234 | 3/1966 | Bond, Jr. et al. | 138/129 |
| 3,252,483 | 5/1966 | Swan | 138/122 |
| 3,565,118 | 2/1971 | Stearns | 138/149 X |
| 4,133,972 | 1/1979 | Andersson et al. | 138/129 X |
| 4,140,154 | 2/1979 | Kanao | 138/122 X |
| 4,380,253 | 4/1983 | Mead et al. | 138/129 X |
| 4,445,543 | 5/1984 | Mead | 138/122 |
| 4,492,089 | 1/1985 | Rohner et al. | 138/149 X |
| 4,510,974 | 4/1985 | Natori et al. | 138/125 X |
| 4,570,679 | 2/1986 | Schippl | 138/149 |

*Primary Examiner*—Stephen Marcus
*Assistant Examiner*—Mark Thronson
*Attorney, Agent, or Firm*—Connolly & Hutz

[57] ABSTRACT

A hose is formed as a spiral component hose of synthetic material, which is surrounded by a gas-tight corrugated hose of fiberglass weave coated with aluminum. The insulation for the hose consists of several sequential layers of synthetic material felts and synthetic material foils, preferably a total of three groups, each consisting of a polyester felt, an interior foil of polyethylene, and an exterior foil of polyethylene terephthalate. The outermost finish consists of a corrugated hose of synthetic material.

7 Claims, 2 Drawing Figures

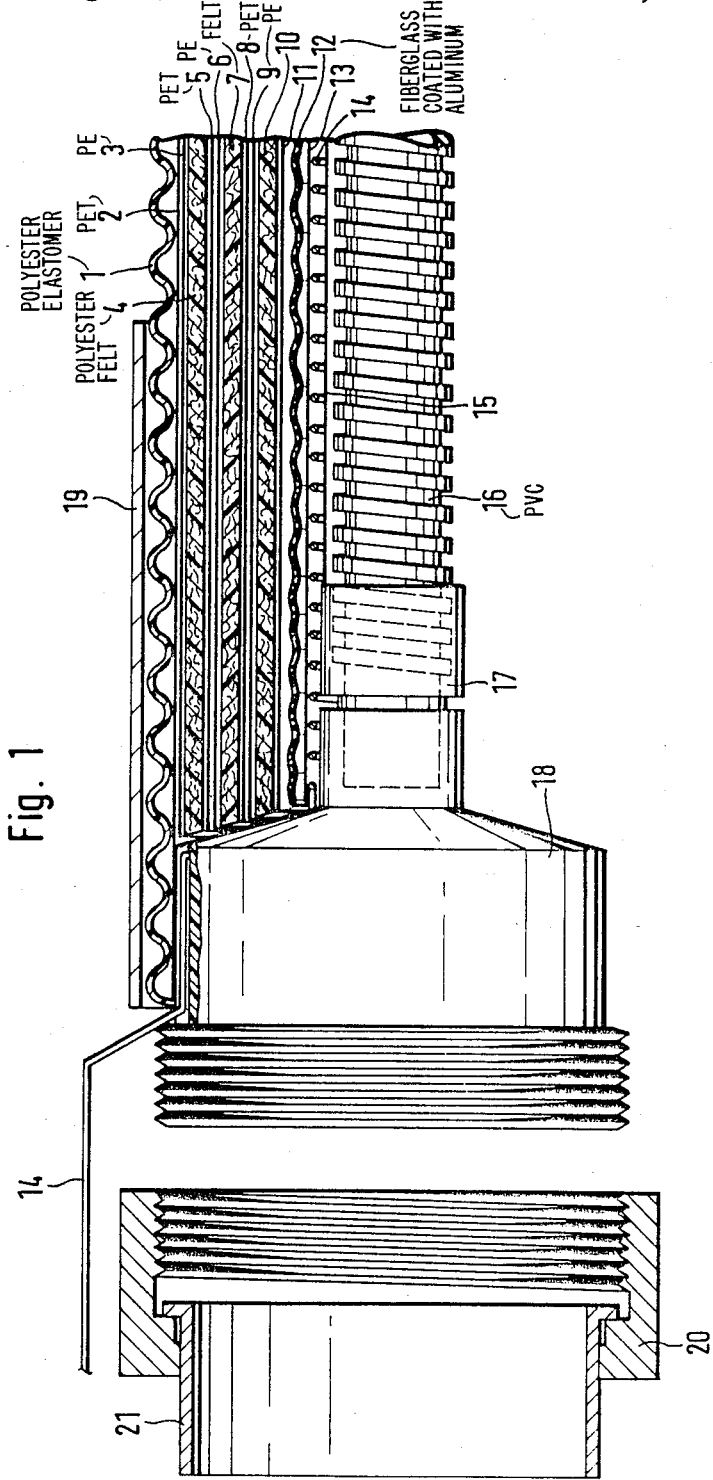

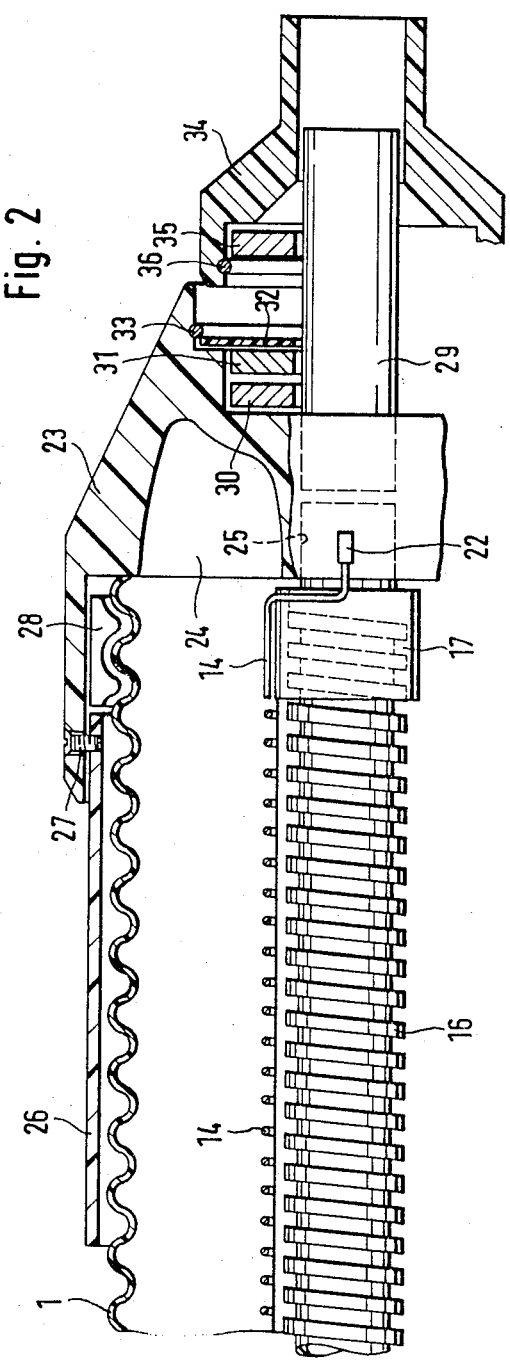

INSULATED HOSE OF SYNTHETIC MATERIAL

BACKGROUND OF THE INVENTION

In recent times, cryotherapy has gained increasing importance in the treatment of rheumatic diseases. Hereby, a preferably dry flow of gas at a temperature as low as −180° C. is applied to the joints or body parts to be treated. According to the functional principle of the equipment used, this gas flow consists of cold air, cold nitrogen gas, or a mixture of the two. In order to guide this cold gas flow to the patient and direct it to the body parts to be treated, a hose is required, which must fulfill a number of specific requirements.

First, the hose must thermally be so well insulated that no significant cooling of the exterior surface of the hose results from the gas throughflow which may be as cold as −180° C. The insulation must be so efficient that practically no water condensation occurs under continuous operation, even at high ambient humidity. Good insulation simultaneously guarantees effective utilization of the refrigerant. In spite of such good insulation, the hose must also have sufficient flexibility at operational temperature, so that the therapist can uniformly and comfortably reach the body regions to be treated without moving the patient. In spite of this high flexibility, however, the hose must also have sufficient mechanical stability. Nor must the weight of the hose be too great, since comfortable handling would be negatively affected by too great weight. Further, it is desirable that the cold capacity of the hose is low, in order to minimize the cooling time and the refrigerant losses. Further, it is also desirable that the hose is inexpensive, i.e. that it can easily be assembled from standard materials. Naturally, these requirements also apply to the hose-end pieces.

The currently used hoses do not fulfill all of these requirements. For instance, an insulation proven in cryotechnology may be glued onto the lines. However, it hardens at low temperatures, so that it is not usable for flexible hoses. If, on the other hand, the hoses are insulated by means of loose bulk insulation material, there is the disadvantage that over time, this material will accumulate in the low-lying areas. Here, the insulation material will be compacted, which causes changes in the insulation properties. The highest incidence of such compacting will naturally occur on hoses that are frequently moved, as is the case in cryotherapy. Superinsulated hoses are too expensive, and their bending radius is too great. Corrugated and smooth tubes of synthetic material also have too great bending radii, disregarding the fact that they will also have to be provided with additional insulation. Corrugated metal tubes have too great cold capacity and are heavy. In addition, they require much space for insulation.

SUMMARY OF THE INVENTION

An object of the invention is to create a treatment hose specifically for cryotherapy which, in addition to being thermally well insulated, is also characterized by high flexibility even at treatment temperature, by low weight, and by low cold capacity, and which is also economical with respect to material and manufacturing.

The hose according to the invention consists exclusively of synthetic materials and is provided with insulation of multilayer structure. Hose or tubing materials are used for the individual layers. This simplifies the assembly. Since exclusively synthetic materials are used, the cold capacity and the weight of the hose are kept low. The individual layers of the insulation are thin or fibrous, which allows high flexibility. Air inclusions, particularly in the fibrous layers, improve the thermal insulation. An aluminum layer reflects the heat radiation penetrating from the outside. The interior hose is a massive hose of synthetic material which thus has sufficient mechanical stability. However, such an interior hose is not in itself sufficiently flexible; it is consequently developed as a spiral component hose. Since a spiral component hose is not gas-tight, the surrounding layers, particularly the corrugated hose of fiberglass, fulfill this function. Surprisingly, it has been found that PVC is excellently suitable as material for the interior spiral component hose, although PVC reputedly has only limited usefulness at low temperatures. The manufacturing of the hose according to the invention is also simple and can be handled without additional fixtures or aids.

The synthetic material hose according to the invention is excellently suitable for use in cryotherapy. However, it is not limited to this application but can be used in any location where deep-cooled gases flow through flexible lines.

THE DRAWINGS

FIG. 1 is a side view partly in section of the end piece of a hose on the machine side in accordance with this invention; and FIG. 2 is a side view partly in section of the end piece of the hose on the handle side, with an attachable nozzle.

DETAILED DESCRIPTION

In the synthetic material hose with the machine end piece shown in FIG. 1, the spiral component hose 16 is the actual synthetic material hose serving for gas transport. It consists of polyvinyl chloride (PVC). Since the spiral component hose 16 is not gas-tight, it is surrounded by a corrugated hose 12 of aluminum coated fiberglass weave. This corrugated hose 12 is sufficiently gas-tight. The aluminum coating prevents penetration of heat radiation from the ambient. Between the spiral component hose and the corrugated hose 12, there are two foils 13, 15, of polyethylene terephthalate (PET). Between the foils 13, 15, there is a cable winding 14 for conduction of electrical signals. These may be, for instance, the signals from a temperature sensor, which is located at the handle end of the treatment hose. The foils 13, 15 and the cable winding 14 are not required for the thermal and mechanical function of the treatment hose.

On the corrugated hose, there is an additional foil 11 of PET. Over this, three groups of synthetic material felt and synthetic material foils are arranged in order to provide additional insulation. Each group consists of a polyester felt 4, 7, 10, an interior foil 3, 6, 9 of polyethylene (PE), and an exterior foil 2, 5, 8 of PET. The exterior surface layer is formed by a corrugated hose of polyester elastomer.

The machine side end piece of the synthetic material hose according to the invention represents a screw element 18 of PVC. The attachment of the spiral component hose 16 to the screw element 18 is achieved by means of a threaded transition piece 17 of PVC. The locking of the corrugated hose 1 onto the screw element 18 is achieved by covering it with a metal sleeve 19 of nickel-plated brass.

The cable winding 14 is brought to the outside through a channel in the screw element 18. The screw element 18 is screwed onto the hose-end piece 21 by means of the screwed sleeve 20.

The total thickness of the synthetic material hose according to the invention is given by the selected thicknesses of the individual layers used. The more groups of synthetic material felts and synthetic material foils are applied for insulation purposes, the better the quality of the insulation. Simultaneously, however, the flexibility of the hose is reduced. A triple grouping of synthetic material felts and synthetic material foils has proven optimal. Thereby, curving radii of approximately 50 cm are possible for a hose with an outside diameter of e.g. 72 mm.

FIG. 2 shows the handle side end piece of the treatment hose. Here, the cable winding 14 ends in a contact piece 22 of a temperature sensor which is located in the hose-end piece 23 of polycarbonate. The hose-end piece 23 has an indentation 24 for purposes of improving the insulation. In addition, the indentation 24 improves the stability with respect to thermal stresses. The hose-end piece 23 has a threading 25, into which the spiral component hose 16 is screwed and where it is locked by means of a transitional threaded piece 17. The spiral component hose 16 is locked into the screw element 18 on the machine side by means of a corresponding transitional threaded piece 17. The hose-end piece 23 accommodates the exterior corrugated hose 1 and a synthetic material tube 26 which is applied thereon. The synthetic material tube 26 constitutes the actual grip surface. It is connected to the hose-end piece by means of three screws 27, which are distributed over the circumference. Optionally, this connection may also be established by means of adhesive. Prior to assembly, two half-shells 28 which are adjusted to the corrugated shape of the hose, are placed over the corrugated hose 1 over a width of 2 to 3 threads in order to lock this unit of synthetic tube 26 and hose-end piece 23 against the corrugated hose 1.

A tube piece 29 is further screwed into the hose-end piece 23. Around the tube piece 29, a soft iron ring 30, an annular permanent magnet 31, and a cover plate 32 of synthetic material are accommodated in indentations in the hose-end piece 23. They are locked in place by means of an annular spring 33.

The nozzle 34, which serves treatment purposes, can be pushed onto the tube piece 29. In the nozzle 34, there is also an annular permanent magnet 35, which is held in place by means of an annular spring 36. The permanent magnet 35 constitutes the antipole to the permanent magnet 31 and renders the adhesion of both parts possible when the nozzle 34 and the hose-end piece 23 are brought into contact with one another. The tube piece 29 is made so long that the cold gas flow is brought as far into the nozzle 34 as possible and so that turbulences are avoided at locations which are not gas-tight.

It is also possible to install pin magnets instead of the annular permanent magnet 31 in the hose-end piece 23, whereby the annular permanent magnet 35 in the nozzle 34 should be retained. With sufficiently strong magnetic force, soft iron material alone is also sufficient as a counterpiece.

The nozzle 34 can be supplemented with reduction pieces and angle pieces at its front opening. Due to the method of locking, the nozzle 34 can easily be turned. The nozzle 34 is made of cold resistant synthetic material; here as well, PVC has surprisingly been found to be suitable.

What is claimed is:

1. Hose of synthetic material for transport of deep-cooled gases, characterized thereby that the hose is formed as a spiral component surrounded by a gas-tight inner corrugation of fiberglass weave coated with aluminum, an insulation around said inner corrugation, said insulation being formed by a plurality of sequential layers of synthetic material foils and synthetic material felts, an exterior corrugation of synthetic material surrounding said insulation, said insulation consists of a plurality of sequential groups of synthetic material foils and synthetic material felts, and each of said groups consisting of a polyester felt, an interior foil, of polyethylene (PE), and an exterior foil of polyethylene terephthalate (PET).

2. Hose of synthetic material according to claim 1, characterized by three groups of synthetic material foils and synthetic material felts.

3. Hose of synthetic material according to claim 2 characterized thereby that said spiral component hose is made of polyvinylchloride (PVC).

4. Hose of synthetic material according to claim 3, characterized thereby that said exterior corrugation is made of polyester elastomer.

5. Hose of synthetic material according to claim 4, characterized thereby that two PET foils with a cable winding for transmission of electrical signals between them are arranged between said spiral component and said gas-tight inner corrugation.

6. Hose of synthetic material for transport of deep-cooled gases, characterized thereby that the hose is formed as a spiral component surrounded by a gas-tight inner corrugation of fiberglass weave coated with aluminum, an insulation around said inner corrugation, said insulation being formed by a plurality of sequential layers of synthetic material foils and synthetic material felts, an exterior corrugation of synthetic material surrounding said insulation, and said exterior corrugation is made of polyester elastomer.

7. Hose of synthetic material for transport of deep-cooled gases, characterized thereby that the hose is formed as a spiral component surrounded by a gas-tight inner corrugation of fiberglass weave coated with aluminum, an insulation around said inner corrugation, said insulation being formed by a plurality of sequential layers of synthetic material foils and synthetic material felts, an exterior corrugation of synthetic material surrounding said insulation, and two PET foils with a cable winding for transmission of electrical signals between them are arranged between said spiral component and said gas-tight inner corrugation.

* * * * *